United States Patent
Gubernick

(10) Patent No.: US 11,628,252 B1
(45) Date of Patent: Apr. 18, 2023

(54) MATERNAL AND FETAL INTRAPARTUM SAFETY MONITOR

(71) Applicant: Martin Gubernick, New York, NY (US)

(72) Inventor: Martin Gubernick, New York, NY (US)

(*) Notice: Subject to any disclaimer, the term of this patent is extended or adjusted under 35 U.S.C. 154(b) by 425 days.

(21) Appl. No.: 16/732,820

(22) Filed: Jan. 2, 2020

Related U.S. Application Data

(60) Provisional application No. 62/788,107, filed on Jan. 3, 2019.

(51) Int. Cl.
| | |
|---|---|
| *A61M 5/172* | (2006.01) |
| *A61B 5/00* | (2006.01) |
| *G16H 40/60* | (2018.01) |
| *G16H 20/17* | (2018.01) |
| *A61K 38/095* | (2019.01) |

(52) U.S. Cl.
CPC ......... *A61M 5/1723* (2013.01); *A61K 38/095* (2019.01); *A61B 5/4356* (2013.01); *A61B 2560/028* (2013.01); *A61M 2205/18* (2013.01); *A61M 2205/3344* (2013.01); *A61M 2205/3561* (2013.01); *A61M 2205/502* (2013.01); *A61M 2205/60* (2013.01); *A61M 2230/63* (2013.01); *G06F 2221/2141* (2013.01); *G16H 20/17* (2018.01); *G16H 40/60* (2018.01)

(58) Field of Classification Search
CPC .. A61B 5/4356; A61B 5/033; A61M 2205/18; A61M 2205/3344
See application file for complete search history.

(56) References Cited

U.S. PATENT DOCUMENTS

| | | | |
|---|---|---|---|
| 6,423,016 B1 | 7/2002 | Hamilton et al. | |
| 6,907,284 B2 | 6/2005 | Hamilton et al. | |
| 9,805,164 B2 | 10/2017 | Hamilton | |
| 2002/0038392 A1* | 3/2002 | De La Huerga | G16H 20/17 710/8 |
| 2005/0177096 A1* | 8/2005 | Bollish | A61B 5/4821 604/65 |
| 2010/0045427 A1* | 2/2010 | Boone, III | G06F 21/31 340/5.23 |
| 2014/0221875 A1 | 8/2014 | Hamilton | |

(Continued)

OTHER PUBLICATIONS

Common Oxytocin Checklist—PeriGen; https://perigen.com/common-oxytocin-checklist/ dated Jan. 10, 2019 (3 pages).

(Continued)

*Primary Examiner* — Bhisma Mehta
*Assistant Examiner* — John J Crawford
(74) *Attorney, Agent, or Firm* — K&L Gates LLP

(57) ABSTRACT

In part, the disclosure relates to a safety monitor and related methods to evaluate and manage intrapartum uterine contractions induced or augmented by Pitocin or other contraction inducing agents. The systems and methods include measuring a contraction parameter that may include one or more of frequency, strength, and duration of uterine contractions through a measurement device connected to a monitor. The systems and methods are programmed to stop the pump-based administration of a contraction inducing agent. Various lock out protocols and control over the ability to re-start a given pump are also described herein.

14 Claims, 7 Drawing Sheets

(56) References Cited

U.S. PATENT DOCUMENTS

| | | |
|---|---|---|
| 2015/0223748 A1 | 8/2015 | Warrick et al. |
| 2016/0270658 A1* | 9/2016 | Ater .................... A61B 5/4356 |
| 2017/0286615 A1 | 10/2017 | Hamilton |
| 2017/0308662 A1 | 10/2017 | Hamilton et al. |
| 2020/0043611 A1 | 2/2020 | Hamilton et al. |
| 2021/0272689 A1 | 9/2021 | Hamilton et al. |

OTHER PUBLICATIONS

How to Add an Oxytocin Checklist to Your EFM System Handout Slides by PeriGen; Apr. 2015 (27 pages).

* cited by examiner

MATERNAL AND FETAL INTRAPARTUM SAFETY MONITOR

CROSS REFERENCE TO RELATED APPLICATIONS

This application claims priority to and the benefit of U.S. Provisional Patent Application No. 62/788,107 filed on Jan. 3, 2019, the entire disclosure of which is incorporate by reference therein.

TECHNICAL FIELD

The technical field generally relates to the monitoring and safeguarding of women in labor and their unborn children. In more detail, the field relates to drug regulation and patient monitoring during labor.

BACKGROUND

Medical professionals use synthetic oxytocin to induce or augment uterine contractions during labor. The F.D.A.-approved synthetic oxytocin, Pitocin, is administered via an intravenous infusion pump. This pump is connected to its own power source and medical professionals turn down (or off) Pitocin manually at their discretion when they perceive the rate of uterine contractions to be excessive. The average patient is administered 4-6 milliunits of Pitocin in order to put them into the active phase of labor.

SUMMARY OF INVENTION

The present invention relates to both uterine contraction monitors and to intravenous infusion pumps for medication to induce and augment labor, and more particularly pertains to the integration of such monitors and pumps through both hardware and software in order to effectively implement safeguards that would protect against brain damage in newborns and postpartum hemorrhage in mothers.

In part, the disclosure relates to a safety monitor and related methods to evaluate and manage intrapartum uterine contractions. Specifically, the frequency, duration or both for a sequence of contractions can be monitored over time. The contraction-related parameters change over time in response to the delivery of contraction inducing drugs such as Pitocin. In part, the disclosure relates to a method of safeguarding mothers and their unborn children during labor. The method may include measuring one or more contraction parameters during a period when a contraction inducing drug is administered to a patient through an intravenous infusion pump. The contraction parameters can include the rate or frequency of contractions, the strength of contractions, and the duration of contractions over a period.

For example, if a patient's contraction has a period of X, if the patient is monitored for a period Y, when the X/Y ratio or percentage is greater than about N, then this may be used as a trigger to turn off the infusion pump. In one embodiment, N ranges from about 0.1 to about 0.7. Thus, for a 30-minute period, if a contraction occupies 15 minutes of the period, N would be 0.5 or 50% of the period. The method may include determining whether the rate of contractions exceed predetermined thresholds. This determination may be based on the contraction frequency, the contraction strength, the contraction duration, fetal heartbeat, maternal heartbeat, and/or changes in any or all of the foregoing inputs. Further, the method may include stopping the intravenous infusion pump from administering a drug when the rate of contractions exceeds a predetermined threshold or a given contraction parameter deviates from its target range. These parameters can be set using evidence-based medicine.

All of the decisions and steps taken with regard to monitoring contractions and contraction inducing drugs, the termination of such drugs, and the restart of delivery of such drugs can be stored to support property compliance with medical procedures. These systems and devices can improve patient outcomes by reducing instances of harm or death to mothers and their infants during labor and delivery worldwide. In so doing, the systems and methods described herein can also drastically reduce the amount of related medical malpractice litigation.

In some embodiments, the intravenous infusion pump receives power through the monitor. In some embodiments, the contraction monitor or the device receiving outputs therefrom is connected to the controls or power supply of the infusion pump such that the pump can be turned off or caused to cease pumping in response to a control signal generated by the detection of an undesirable contraction state.

In one aspect, the disclosure relates to a method, device, and system for administering a medication, the method, device, and system comprising a maternal fetal monitor comprising a contraction measurement device configured or operable to measure rate of uterine contractions and a user interface configured or operable to display the rate of uterine contractions and an intravenous infusion pump configured or operable to administer a medication intravenously to a patient, wherein the rate of uterine contractions comprises frequency, strength, and duration of uterine contractions, wherein the intravenous infusion pump administers the medication to induce and augment uterine contractions, and wherein the device stops the administrations of the medication when the rate of uterine contractions is outside a predetermined range.

A system of one or more computers can be configured or operable to perform particular operations or actions by virtue of having software, firmware, hardware, or a combination of them installed on the system that in operation causes or cause the system to perform the actions. One or more computer programs can be configured or operable to perform particular operations or actions by virtue of including instructions that, when executed by data processing apparatus, cause the apparatus to perform the actions. One general aspect includes a device including: a maternal fetal monitor including: a contraction measurement device configured or operable to measure a rate of uterine contractions, and a user interface configured or operable to display the rate of uterine contractions. The device also includes an infusion pump configured or operable to administer a medication intravenously to a patient.

In one embodiment, the rate of uterine contractions is selected from the group including of frequency, strength, and duration of uterine contractions. In one embodiment, the infusion pump administers the medication intravenously to induce and augment uterine contractions. Further, in one embodiment the device stops the administration of the medication when one or more of the frequency, strength, or duration of uterine contractions is outside predetermined ranges. Other embodiments of this aspect include corresponding computer systems, apparatus, and computer programs recorded on one or more computer storage devices, each configured or operable to perform the actions of the methods. Various software modules for triggering based on thresholds being met or exceeded can also be used with various embodiments.

Implementations may include one or more of the following features. In one embodiment, the device measures frequency, strength, and duration of uterine contractions at predetermined intervals. In one embodiment, the measurement device measures pressure across a patient's abdomen. In one embodiment, the measurement device is a tocodynamometer belt or intrauterine pressure catheter. In one embodiment, the infusion pump is connected to the patient via an intravenous catheter. In one embodiment, the medication is Pitocin or another form of synthetic oxytocin. In one embodiment, the device is further connected to a remote terminal, the remote terminal including an alarm that sounds both at external locations and in the patient's room when the rate of uterine contraction falls outside the predetermined ranges. In one embodiment, the device sounds an alarm at a remote nurses' station.

In one embodiment, the device controls the power source to the intravenous infusion pump. In one embodiment, the device would automatically shut off the power to the infusion pump when a patient is contracting for more than 50 percent of a predetermined period of time. In one embodiment, passcodes corresponding to categories of medical staff delineated by seniority and expertise such that each category has a set number of times to restart the pump, once the set number of times is met within a category, the pump cannot be turned on by a member of that category. In one embodiment, the strength of contraction is measured from a baseline when the uterus is relaxed to the peak of a contraction. In one embodiment, the contraction measurement device measures the strength of contraction by measuring one or more pressure values in or from the uterus. In one embodiment, the contraction measurement device measures the strength of contraction by measuring one or more pressure values in or from the uterus such as in mm Hg or other units of pressure. Implementations of the described techniques may include hardware, a method or process, or computer software on a computer-accessible medium.

One general aspect includes a system or adapter for an existing system in which a device includes a controller and code recognition system to turn the infusion pump back on by means of inputting private access codes. Other embodiments of this aspect include corresponding computer systems, apparatus, and computer programs recorded on one or more computer storage devices, each configured or operable to perform the actions of the methods.

One general aspect includes a method for the safe administration of contraction inducing drugs including: administering a contraction inducing drug intravenously to a patient through an intravenous infusion pump; measuring one or more of frequency, strength, and duration of uterine contractions through a measurement device connected to a monitor; determining whether one or more of the measured frequency, strength, or duration of uterine contractions exceeds predetermined thresholds; and stopping the intravenous infusion pump from administering a drug when the frequency, strength, or duration of uterine contractions exceed the predetermined thresholds, where the infusion pump receives power through the monitor, and where the infusion pump is stopped by shutting down the power supply from the monitor. Other embodiments of this aspect include corresponding computer systems, apparatus, and computer programs recorded on one or more computer storage devices, each configured or operable to perform the actions of the methods.

Implementations may include one or more of the following features. The method further including sending an alarm notification to a remote terminal when a predetermined threshold is exceeded. The method further including restarting the intravenous administration of the drug through the infusion pump by entering a passcode. The method where users are limited to a fixed number of passcode entries based on the user's seniority and expertise. The method where the infusion pump is administering a contraction inducing drug intravenously to the patient. The method where the contraction inducing drug is Pitocin or another form of synthetic oxytocin. The method may include measuring the strength of a contraction from a baseline when the uterus is relaxed to the peak of a contraction. The method may include determining the strength of contraction by measuring one or more pressure values in or from the uterus. Implementations of the described techniques may include hardware, a method or process, or computer software on a computer-accessible medium.

One general aspect includes the method further including measuring one or more pressure values in or from the uterus such as in mm Hg or other units of pressure. Other embodiments of this aspect include corresponding computer systems, apparatus, and computer programs recorded on one or more computer storage devices, each configured or operable to perform the actions of the methods.

Although, the disclosure relates to different aspects and embodiments, it is understood that the different aspects and embodiments disclosed herein can be integrated, combined, or used together as a combination system, or in part, as separate components, devices, and systems, as appropriate. Thus, each embodiment disclosed herein can be incorporated in each of the aspects and features to varying degrees as appropriate for a given implementation. Further, the various apparatuses, pumps, sensors, software, thresholds, measurement devices, controllers, monitors, components and parts disclosed herein and other apparatus and assemblies described herein can be used with existing patient and baby monitoring systems as add on components or as separate systems and with other methods without limitation.

DETAILED DESCRIPTION

Figure 1:
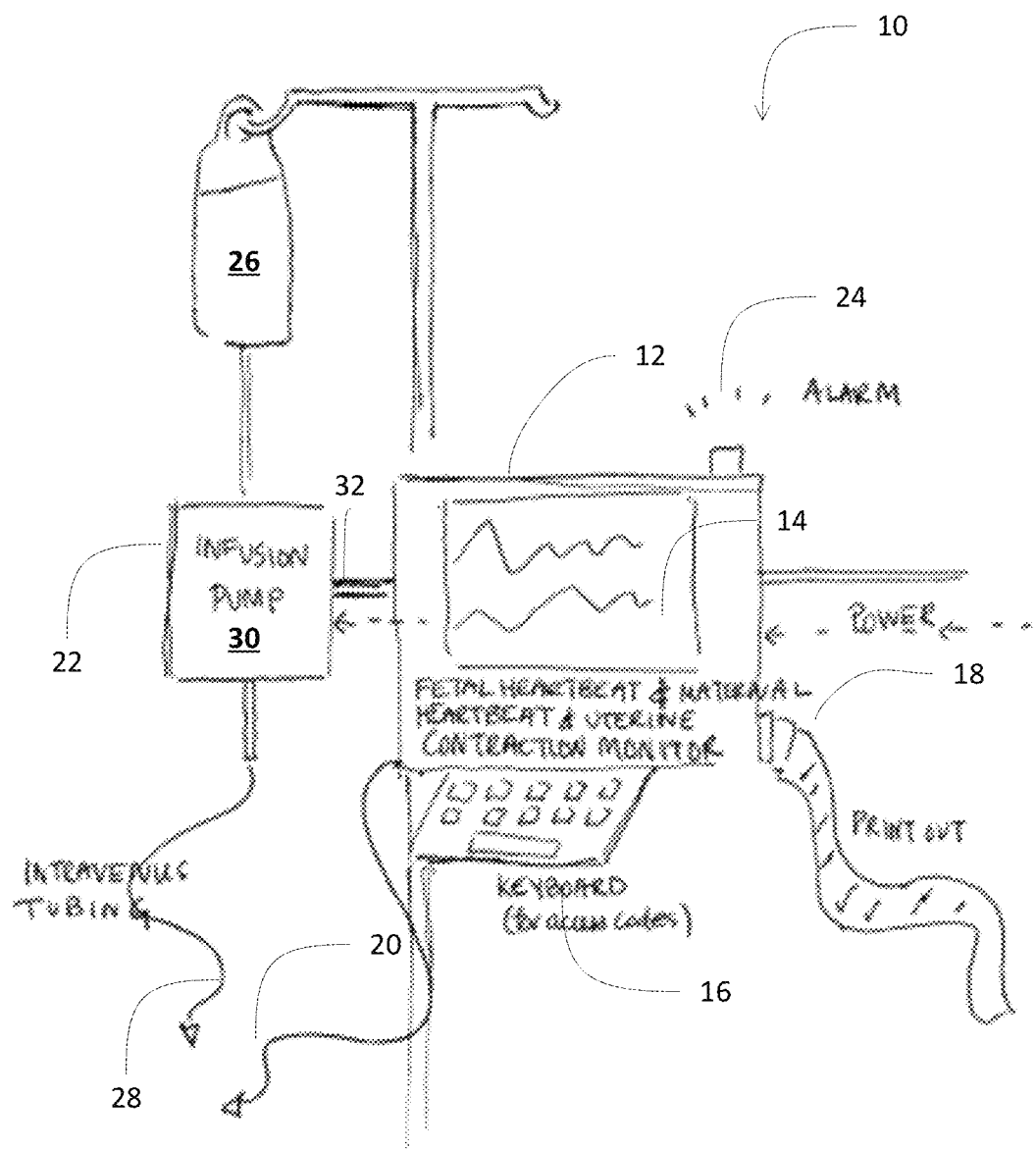
FIG. 1 depicts an example system that monitors drug administration to a patient according to an illustrative embodiment of the disclosure.

In the following detailed description, reference is made to the accompanying drawings, which are herein included as a portion of the present disclosure. In the drawings, similar symbols and reference characters typically identify similar components throughout the several views, unless context dictates otherwise. The illustrative aspects described in the detailed description, drawings, and claims are not meant to be limiting. Other aspects may be utilized, and other changes may be made, without departing from the scope of the subject matter presented in the present disclosure.

Currently, medical professionals use monitors that track the heart rate of the fetus during labor as well as the rate of contraction in the mother. However, while these monitors are equipped to alert a medical professional if the fetal heart rate is outside of the normal range by means of an alarm, they do not trigger alarms if the mother's contraction rate falls outside the normal range. These systems also do not contain automatic safeguards to protect maternal and fetal health, such as an automatic shut-off of drug administration pumps when there is an alarm-causing event. These individual devices, widely used in the labor and delivery medical field, are each lacking due to their inability to communicate with one another. A vital need remains for an invention that would integrate these two existing devices by connecting the contraction inducing drug pump to the monitor and to improve on them by incorporating software that would recognize excessive uterine contractions and prevent medical professionals from continuing to administer contraction inducing drugs when the uterine contraction rate falls outside of the pre-determined, safe ranges.

Conventionally, the labor and delivery medical community consistently faces a problem of excessive uterine contractions caused by inappropriate intravenous doses of a contraction inducing drug, which puts both baby and mother at risk. Typically, the contraction inducing drug is Pitocin, a synthetic form of oxytocin. Contraction inducing drugs dramatically affect the rate of uterine contractions. Excessive uterine contractions over time can cause brain damage in newborns and, in the extreme cases, fetal death. In mothers, excessive uterine contractions can cause postpartum hemorrhage, which can lead to a loss of uterus or infertility.

The disclosure is directed to systems and methods to reduce the risks associate with extended use of contraction inducing drugs by monitoring one or more parameters of one or more patients, which may include a mother and/or an infant. The disclosure is directed to systems and methods for regulating the ability of medical personnel to make changes to the delivery system to affect the distribution and/or usage of contraction inducing drugs, and other similar compounds, to a patient. In many embodiments, affecting the distribution and/or usage of contraction inducing drugs, and other similar compounds, may include regulating control of the delivery system and/or regulating access to the delivery system. These systems and methods would enable limiting the amount of contraction inducing drugs administered intravenously over extended periods of time to mothers who are experiencing adverse reactions to the contraction inducing drugs. In some instances, an adverse reaction may include a mother having uterine contractions at an excessive rate. In other instances, an adverse reaction may include a mother having strong uterine contractions where each contraction occurs for an extended period of time.

In a brief overview, a system in accordance with the present disclosure is shown in FIG. 1. As shown in FIG. 1, the system 10 includes a maternal fetal monitor 12. The monitor 12 includes a user interface 14 that that is enabled to connect to a server through either a wired or wireless connection. The monitor 12 is enabled to display various metrics of the mother and/or fetus on the user interface 14 including, but not limited to, frequency of contraction, strength of contraction, duration of contraction, maternal heart rate, fetal heart rate, oxygen saturation, temperature, blood pressure, or any other suitable metric. The monitor 12 is enabled to display one or more types of data recorded and/or retrieved from one or more placed sensors. Various embodiments of the system 10 are shown in different figures. Various components and iterations and connections of the exemplary systems shown may be combined or omitted in various embodiments.

In some embodiments, the monitor's interface may display the maternal heart rate pattern, the fetal heart rate pattern, and the hills and valleys of the contractions—which reflect the contractions' frequency, strength, and duration. The monitor 12 may include a keyboard 16 and a printer 18 to print a hard-copy of any selected period. In many embodiments, the keyboard 16 may be used for data entry and/or notes associated with the one or more types of data recorded and/or retrieved from the one or more placed sensors. In various embodiments, the keyboard 16 may be used for entering access codes which may enable one or more doctors, nurses, and/or other medical professionals to access capabilities of the monitor 12.

Figure 2:
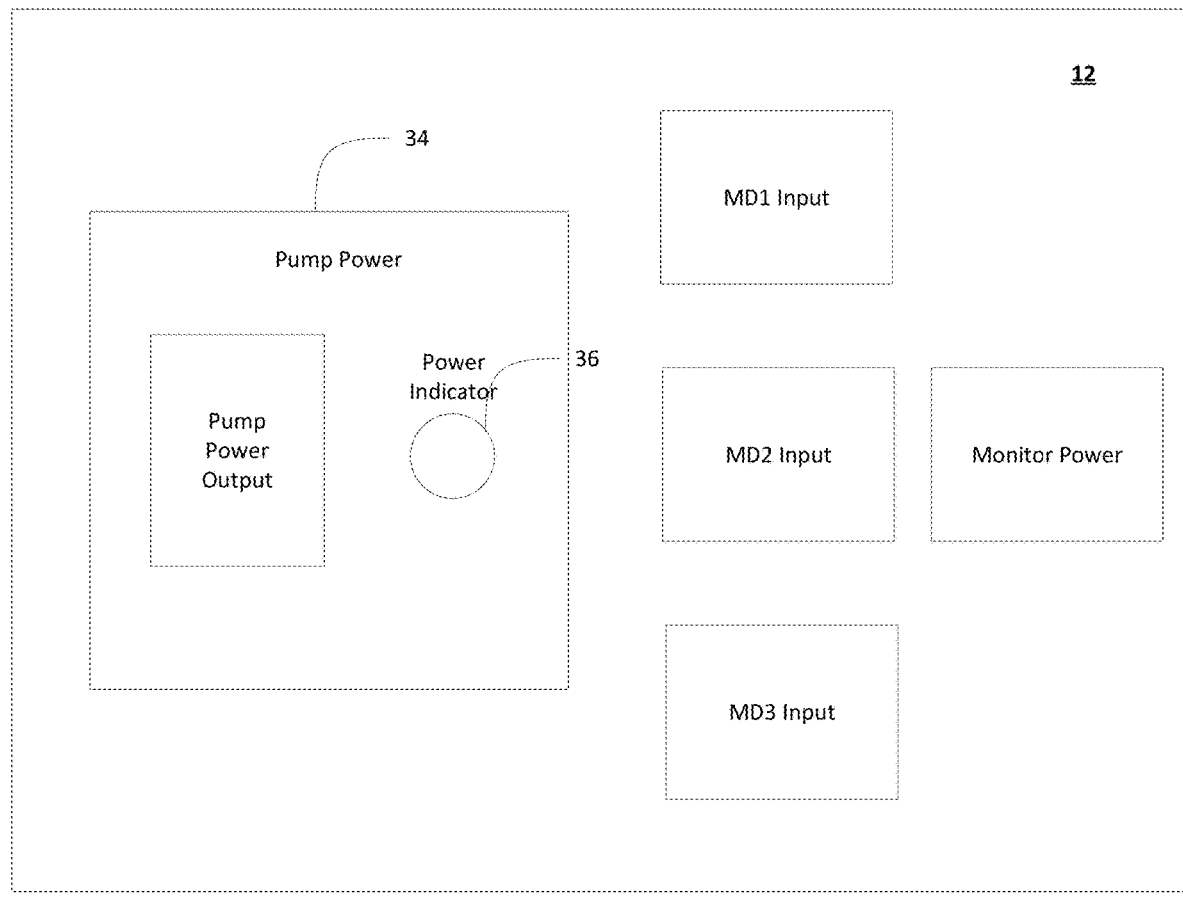
FIG. 2 depicts the inputs and outputs of a monitor in the system according to an illustrative embodiment of the disclosure.
Figure 3:
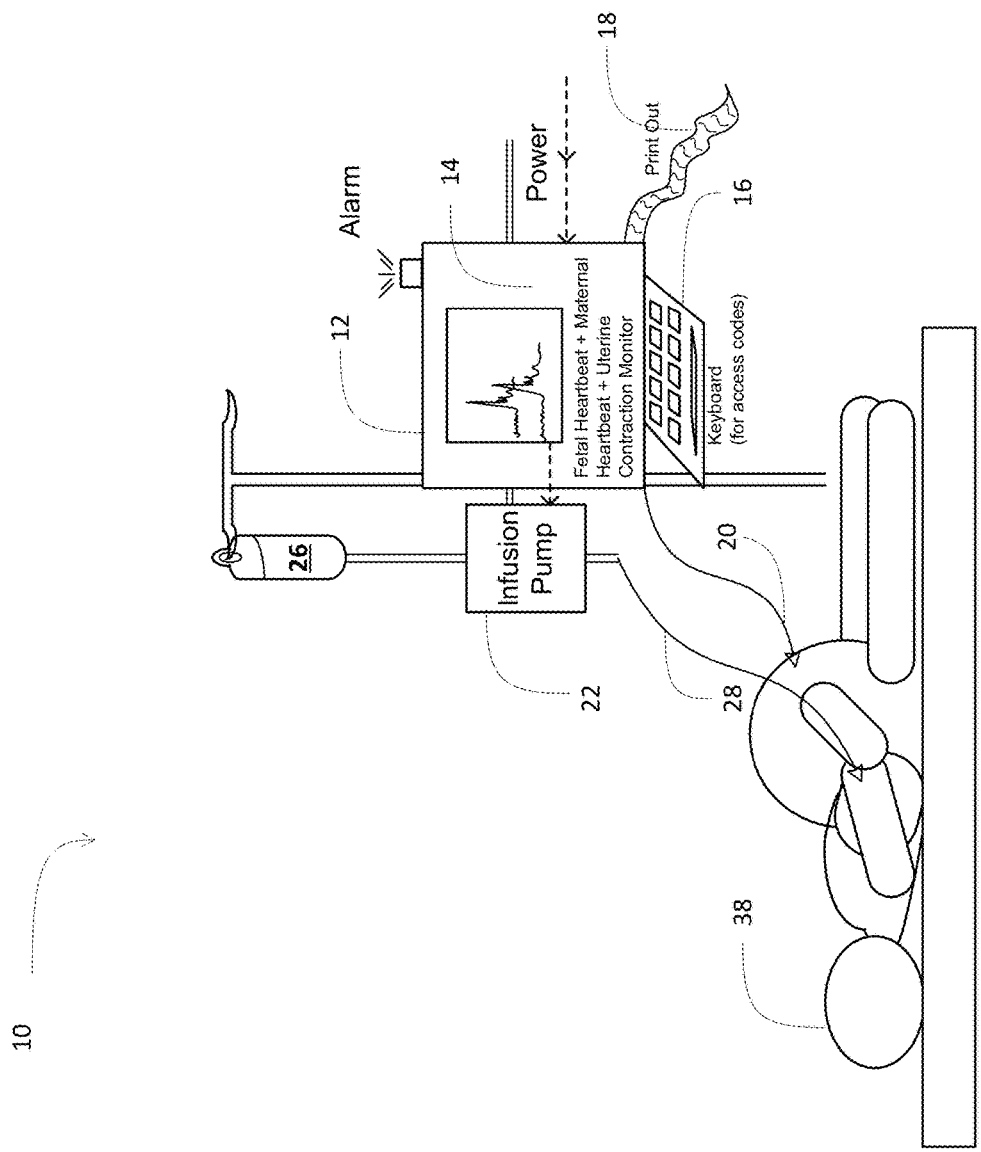
FIG. 3 depicts the exemplary system connected to a patient according to an illustrative embodiment of the disclosure.

The monitor 12 includes a measurement device 20 that is enabled to be placed on an abdomen of a patient or in the uterus, as seen in FIG. 3. In one embodiment, the measurement device 20 includes a tocodynamometer ("toco belt"), intrauterine pressure catheter, or both, to measure the selected metrics, such as frequency, strength, and duration of contraction. Both devices may measure the pressure against the intrauterine wall, ultrasound signals, or voltage changes in the uterine wall when the uterus contracts. In some embodiments, the measurement device 20 may include an ultrasound transducer to measure ultrasound signals. In other embodiments, the measurement device 20 may further comprise electrodes attached to the patient. The electrodes may measure electrical/voltage signals across the patient's abdomen to detect desired metrics, such as heart rate. The measurement device 20 may be connected to the monitor 12 through a wired or wireless connection. The one or more measurement devices are connected to the monitor via one or more input ports MD1, MD2, MD3, as seen in FIG. 2. The measurement device 20 sends values for each measured metric to the monitor 12 for display on the interface 14.

In operation, the system 10 uses one or more of the measurement devices 20 to measure a patient's contraction rate, including frequency, strength, and duration of contraction. When the rate of contraction exceeds predetermined thresholds, the system 10 shuts off the intravenous infusion pump 22 and stops administration of the contraction inducing drug. The system 10 may notify a medical professional of the shutoff at the monitor 12, at a remote terminal, or both using the alarm 24. The caring medical professional is enabled to restart the intravenous infusion pump 22 by entering a passcode on the keyboard 16.

In many embodiments, each medical professional may be assigned a unique passcode that may enable each medical professional to override a shutoff of the intravenous infusion pump 22. The system 10 is enabled to associate a given passcode with an ability to override a shutoff a specified number of times. The specified number of times a user may enter an override passcode is defined in the system 10 based on the user's rank and seniority. In many embodiments, a nurse and/or an intern may be enabled to override a shutoff once or twice, whereas more senior staff would be authorized additional overrides based on their positions and expertise. The number of pre-determined overrides may vary depending on level of expertise and institutional preferences.

In some embodiments, the system 10 may allow a single user to set normal/safe ranges for multiple monitors through a central computing device. In other embodiments, the system 10 may calculate an individual patient's normal/safe ranges based on patient information that was previously entered. For example, if a patient has a low resting heart rate, the system may account for that anomaly when selecting a normal/safe maternal heart rate threshold. The monitor 12 may then take action if the measured values fall outside the normal/safe threshold ranges for that specific patient. In some embodiments, the system 10 may include a plurality of thresholds, denoting various levels of breaches. For example, one threshold may indicate a warning alarm, a second threshold may define a danger limit and result in shutoff, and a third threshold may define a life-threatening breach and trigger the requirement of a code input.

The system 10 further includes an intravenous infusion pump 22 to administer contraction inducing drugs to the patient, shown in FIGS. 1 and 3. The pump includes a bag 26 containing a fluid with a contraction inducing drug that may be administered intravenously, an intravenous catheter 28, a control box 30 that powers the pump, and a power input 32. The power input 32 is connected to the monitor 12, and can be turned off at a threshold breach. The control box 30 may be used by a medical professional to select the amount and rate of drug administration through the pump 22. The intravenous catheter 28 is connected to the patient through a vein in the patient's arm or at any other suitable location. The contraction inducing drug is administered to the patient from the bag 26 through the control box 30 and then through the intravenous catheter 28 to the patient.

As seen in FIG. 2, the intravenous infusion pump's control box 30 is connected to the monitor 12 through a wired connection at the back of the monitor. The intravenous infusion pump 22 receives its power through the port/connection device/34 of the monitor 12. When the intravenous infusion pump 22 is receiving power from the monitor 12 an indicator 36 may be lit to show that the power is on. When the monitor 12 detects a threshold breach, the monitor 12 may immediately turn off power to the pump 22 and thereby stop the administration of the contraction inducing drugs. In some embodiments, the pump 22 is integrated into the monitor 12 forming a single device. In other embodiments, the pump 22 may be a separate device that is connected to the monitor 12 through a detachable/pluggable connection device 34.

Figure 4:
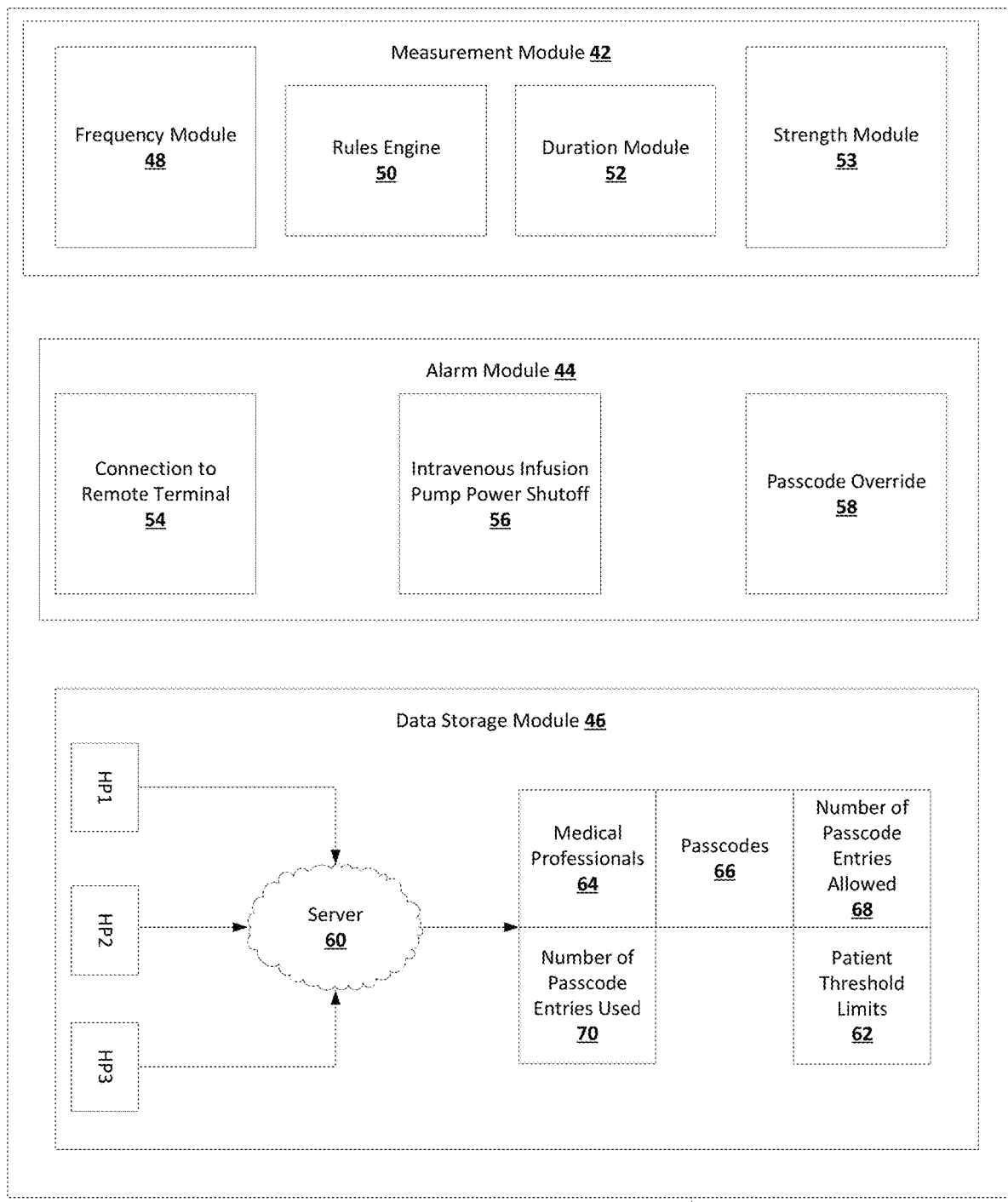
FIG. 4 depicts an example of the software architecture of the system according to an illustrative embodiment of the disclosure.

FIG. 4 depicts an example embodiment of an implementation of the system. As shown in FIG. 4, the system 40 includes a measurement module 42, an alarm module 44, and a data storage module 46. The measurement module 42 may include a frequency module 48, a duration module 52 and a strength module 53 to detect frequency, duration and/or strength of uterine contractions respectively. The measurement module 42 may further include a rules engine 50 to compare the detected frequency, duration, and strength values with a predetermined threshold. The system may further include an alarm module 44. The alarm module may be enabled to shut off power from the monitor 12 to the intravenous infusion pump 22 when a threshold breach is detected 56. The alarm module 44 may also send an alarm notification to a remote terminal through a wireless connection 54. The alarm module 44 may be enabled to receive inputs from a connection to a remote terminal 54 to allow a medical professional to enter a passcode to override a pump shutoff 58.

The system 40 includes a data storage module 46 that may be integrated across one or more hospitals. In many embodiments, the data storage module 46 may work in conjunction with one or more monitors 12 which may reside in one or more hospitals. The data storage module 46 may include a server 60 that is capable of receiving information from a plurality of hospitals HP1, HP2, HP3. The server 60 may include the data of each monitor's predetermined thresholds 62, each medical professional in each hospital that may monitor a labor and delivery patient 64, the passcode associated with each medical professional in the system 66, and the number of shutoff overrides prescribed by each hospital for each passcode/medical professional 68. The system further includes data related to the number of times a particular passcode has already been entered at a particular monitor 70.

Figure 5:
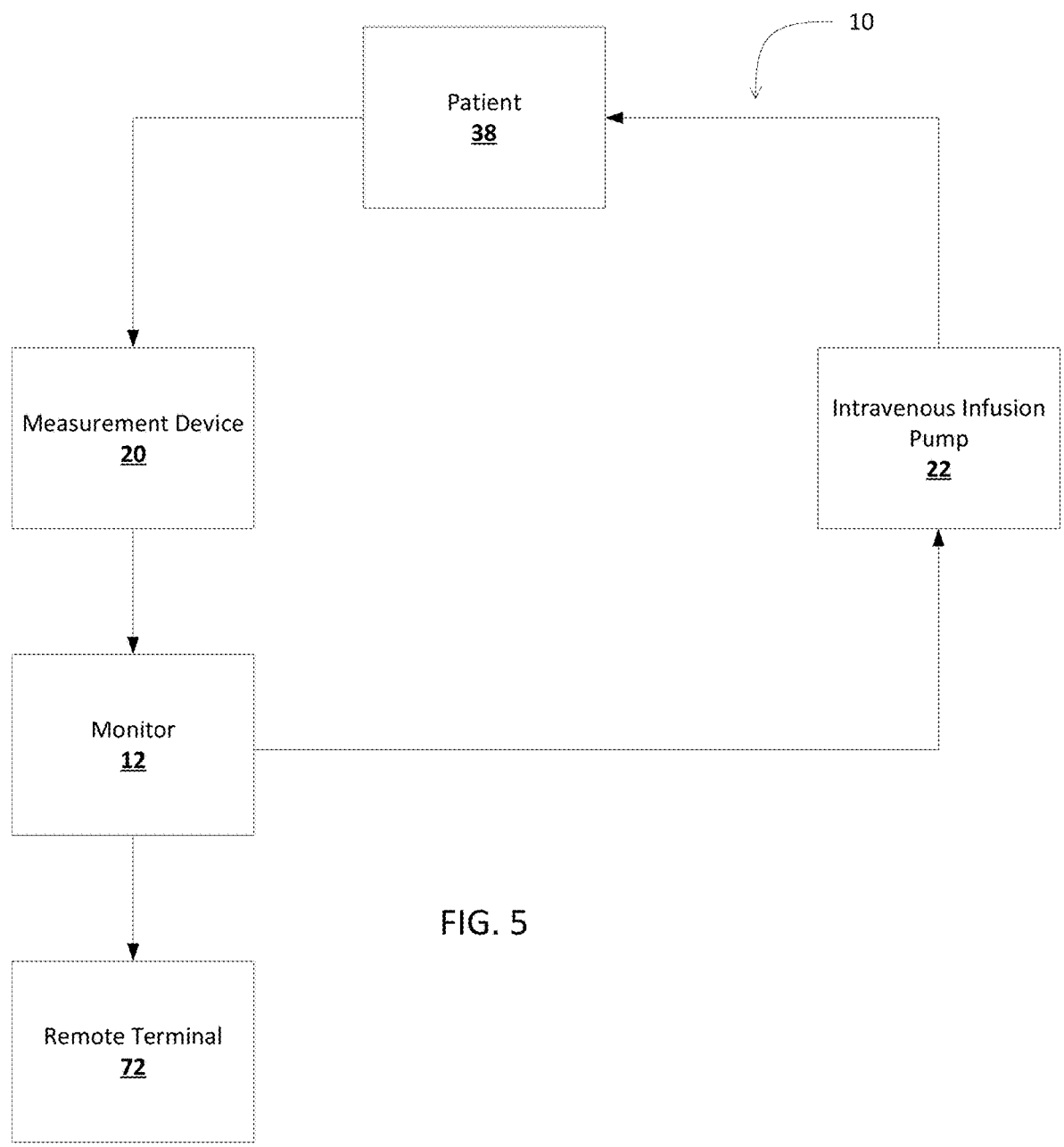
FIG. 5 is a block diagram of the system in operation according to an illustrative embodiment of the disclosure.

FIG. 5 illustrates a block diagram of the system in action. The patient 38 is connected to a measurement device 20 and an intravenous infusion pump 22. The pump 22 administers a contraction inducing drug to the patient 38. The pump is connected to a monitor 12 and receives power from the monitor 12. While the patient 38 is in labor and experiencing contractions, the measurement device 20 measures the patient's rate of contractions including frequency, strength, and duration of the contractions. Data from the measurement device 20 are sent to the monitor 12 for processing and display. The monitor 12 compares the measured values to one or more predetermined thresholds. When the measured values exceed a threshold, the monitor emits an alarm notification at a remote terminal 72. The monitor 12 is enabled to shut off the power to the pump 22. In some embodiments, a monitor may simultaneously emit an alarm notification and shutoff power to the pump. In some embodiments, depending on which threshold has been exceeded, a monitor may solely emit an alarm notification.

In some embodiments, the system may be connected to a separate remote terminal in the hospital, such as a nurses' station. A medical professional may be enabled to monitor measurements and alarms from the system 10 at the remote terminal. Upon being notified of an alarm, the medical professional may then enter a passcode on the monitor 12 via the keyboard 16 to override the shutoff of the infusion pump 22. The system 10 may send data from the monitor 12 to this remote terminal over a wireless connection. In some embodiments, the data may include one or more metrics displayed on the monitor. In other embodiments, the data may only include an alarm for a threshold breach. In many embodiments, a monitor may alert a medical professional of the potential danger to the mother and fetus by triggering an alarm at a remote terminal, such as a nurses' station as well as in the labor and delivery room.

The intravenous infusion pump would be able to be switched back on by means of passcodes inputted to a software system on the monitor. Medical professionals at each hospital may be assigned codes to the system corresponding to their respective ranks, seniorities, and expertise. In one embodiment, a hospital administrator may be enabled to select a number of times that a passcode may be utilized. In other embodiments, the system evaluates a user's rank, seniority, expertise, and any other relevant factor to determine how many entries a user is allowed. For example, a nurse or intern may be allowed one or two entries, a resident may be allowed four entries, an attending may be allowed six entries, and the head of the department may be the only person who is allowed unlimited entries.

The system will prescribe and limit how many times a medical professional may override a shutoff of an intravenous infusion pump. After a medical professional has reached their override limit to turn the pump back on, the medical professional would have to seek out a senior ranking member of staff to put in their own access codes to turn the pump back on. The head of the department or the institution may be the only person who is able to override the safety lock altogether and keep the pump on continuously or attach it to an alternative power source. In some embodiments, surpassing a specified number of overrides may lock out all of the users of a particular category. For example, if a nurse A restarts a pump 1 time to deliver the contraction inducing drug, the system would allow one more nurse, such as nurse B, to restart the pump one more time, but after that, all nurses, Nurse A to Nurse Z would be locked out and prevented from turning the pump back on. This category-based approach would ensure that more senior medical professionals would be notified and consulted at the appropriate times.

In many embodiments, the system is enabled to create categories of users. Categories of users may be enabled to access a pool of available override uses for each system. For example, in one embodiment, all nurses may have a combined 2 overrides for a single intravenous infusion pump. If both overrides have been used, a nurse would have to get approval from a higher-ranking member of the medical staff.

Figure 6A:
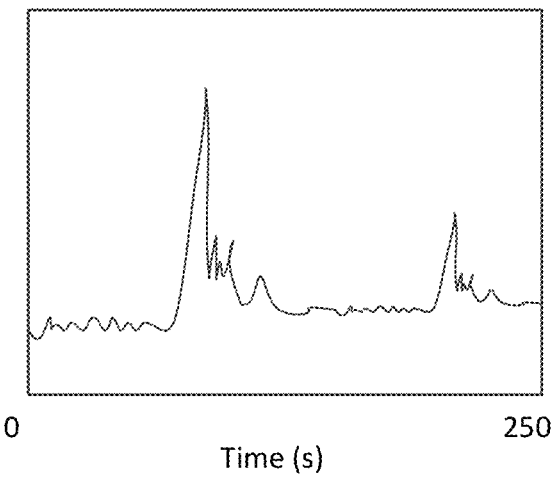
FIGS. 6A and 6B depicts exemplary contractions waveforms that may be measured by the system according to an illustrative embodiment of the disclosure.
Figure 6B:
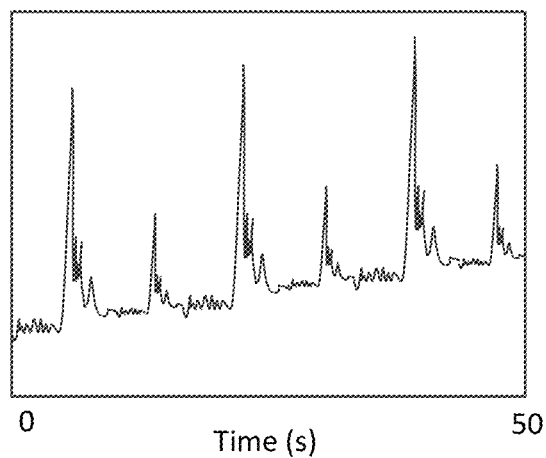

FIGS. 6A-B provide examples of contractions that may be measured by the system. FIG. 6A depicts normal contraction measurements. FIG. 6B depicts contraction measurements that may cause an alarm event. As shown in FIG. 6B, the rate of contractions is fifteen times greater than a normal rate of contraction, such as shown in FIG. 6A. In the embodiment shown in FIG. 6B, the rate of contractions greatly exceeds the normal rate of contraction (as shown in FIG. 6A) and the system will automatically respond by shutting off the intravenous infusion pump connected to the monitor and stop the administration of contraction inducing drugs to the patient.

Figure 7:
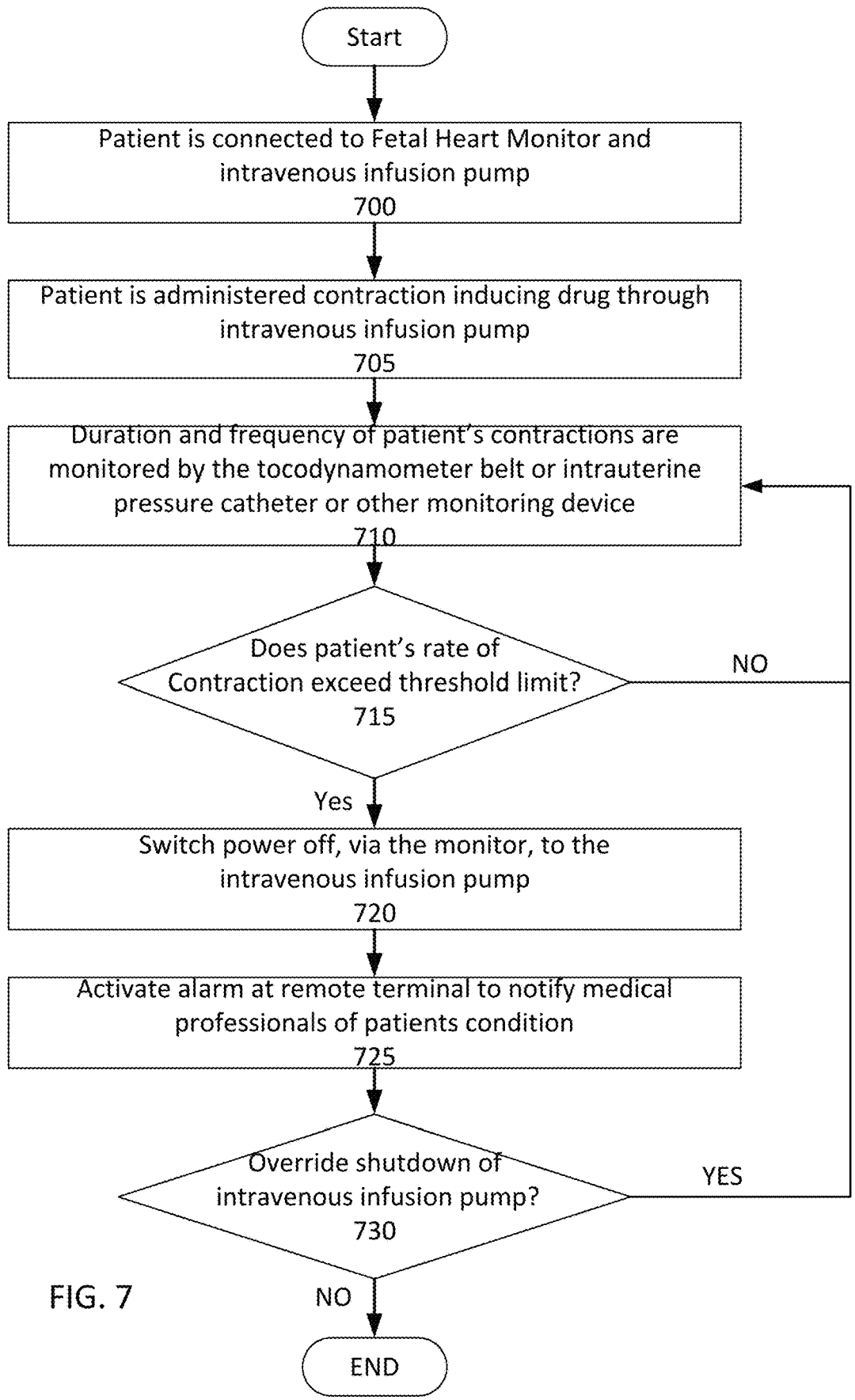
FIG. 7 is a flow chart illustrating an example process of monitoring contraction inducing drug administration according to an illustrative embodiment of the disclosure.

FIG. 7 depicts a flow chart of how the system may be used to monitor the administration of contraction inducing drugs. When a patient is admitted for labor and delivery, the patient and fetus are monitored using a maternal fetal monitor (step 700) and contraction inducing drugs are administered through an intravenous infusion pump (step 705). A measurement device is placed on the patient's abdomen or in the uterus to monitor the frequency, strength, and duration of contractions, as well as maternal and fetal heart rates (step 710). In one embodiment, the step includes monitoring duration and frequency of patient's contractions by a tocodynamometer belt or intrauterine pressure catheter or other monitoring device (step 710). A medical professional selects one or more threshold limits for safe frequency of contractions, strength of contractions, duration of contractions, maternal heart rate, and fetal heart rate on the corresponding monitor. In many embodiments, a pump may administer contraction inducing drugs until the frequency of contractions and/or strength of contractions and/or duration of contractions exceeds one or more of the threshold limits. In some embodiments, a threshold limit may be if the frequency and/or strength and/or duration of contractions is greater than a specified rate. In some embodiments, the intravenous infusion pump may be shutoff in response to exceeding a threshold limit.

The system continuously monitors the maternal frequency, strength, and duration of contractions as well as the maternal and fetal heart rates on the monitor (Step 715). If a patient's frequency, strength, and/or duration of contractions do not exceed the predetermined threshold limits, the monitor will continue monitoring (Step 710). If the uterine contraction rate fall outside the predetermined thresholds, the system will automatically shut off the power to the connected intravenous infusion pump (step 720). An alarm is activated at a remote terminal to notify the caring medical professionals that a threshold breach has been detected by the monitor (step 725).

If the caring medical professional decides to override the shutoff of the intravenous infusion pump (step 730), the medical professional may enter their designated passcode to restart the power to the infusion pump, and, at that point, the monitor will continue monitoring the patient and continue powering the intravenous infusion pump (step 710). Otherwise, the power to the intravenous infusion pump will remain shut off. In some embodiments, the caring medical professional is notified of the threshold breach before the pump is shutoff. The medical professional can then enter their designated passcode to override the breach before the intravenous infusion pump is shutoff. In one embodiment, the system may take other suitable actions in response to a threshold breach. For example, in one embodiment, the system may automatically reduce the pump's dosage of the contraction inducing drug rather than shutting off the pump altogether.

In terms of Pitocin, there are no ill side effects of stopping the pump for the mother or fetus other than potentially slowing the time of delivery. The half-life of Pitocin is 1 minute 30 seconds. Upon stopping the intravenous infusion pump, Pitocin leaves the patient's body within five (5) minutes and the increased rate of contraction caused by the drug is neutralized. Therefore, timely adjustments to Pitocin or some other contraction inducing drug may have a near-immediate impact.

The disclosure provides a technical solution to reduce and/or prevent the occurrence of newborn brain damage, death, incapacity, and other outcomes associated with prolonged exposure to excessive contractions caused by the excessive use of contraction inducing drugs.

In many embodiments, this system may significantly decrease the instances of brain damage or morbidity in newborns as well as incidents of maternal uterine hemorrhage and related health problems by the tens of thousands around the world. In so doing, the invention could reduce the medical liability issues related to such disasters by billions of dollars in the United States alone. Beyond the financial implications, the potential benefit to society from such an system is immeasurable.

The description is intended to provide an overview of device hardware and other operating components suitable for performing the methods of the disclosure described herein. This description is not intended to limit the applicable environments or the scope of the disclosure. Similarly, the hardware and other operating components may be suitable as part of the apparatuses described above. The disclosure can be practiced with other system configurations, including personal computers, multiprocessor systems, microprocessor-based or programmable electronic device, network PCs, minicomputers, mainframe computers, and the like.

Some portions of the detailed description are presented in terms of algorithms and symbolic representations of operations on data bits within a computer memory. These algorithmic descriptions and representations can be used by those skilled in the computer and software related fields. In one embodiment, an algorithm is here, and generally, conceived to be a self-consistent sequence of operations leading to a desired result. The operations performed as methods stops or otherwise described herein are those requiring physical manipulations of physical quantities. Usually, though not necessarily, these quantities take the form of electrical or magnetic signals capable of being stored, transferred, combined, transformed, compared, and otherwise manipulated.

Unless specifically stated otherwise as apparent from the following discussion, it is appreciated that throughout the description, discussions utilizing terms such as "processing" or "computing" or "correlating" or "detecting" or "measuring" or "calculating" or "comparing" "generating" or "sensing" or "determining" or "displaying," or Boolean logic or other set related operations or the like, refer to the action and processes of a computer system, or electronic device, that manipulates and transforms data represented as physical (electronic) quantities within the computer system's or electronic devices' registers and memories into other data similarly represented as physical quantities within electronic memories or registers or other such information storage, transmission or display devices.

The present disclosure, in some embodiments, also relates to apparatus for performing the operations herein. This apparatus may be specially constructed for the required purposes, or it may comprise a general purpose computer selectively activated or reconfigured by a computer program stored in the computer. Various circuits and components thereof can be used to perform some of the data collection and transformation and processing described herein.

The algorithms and displays presented herein are not inherently related to any particular computer or other apparatus. Various general purpose systems may be used with programs in accordance with the teachings herein, or it may prove convenient to construct more specialized apparatus to perform the required method steps. The required structure for a variety of these systems will appear from the description below. In addition, the present disclosure is not described with reference to any particular programming language, and various embodiments may thus be implemented using a variety of programming languages. In addition, where the use of the term "about" is before a quantitative value, the present teachings also include the specific quantitative value itself, unless specifically stated otherwise.

The terms "about" and "substantially identical" as used herein, refer to variations in a numerical quantity that can occur, for example, through measuring or handling procedures in the real world; through inadvertent error in these procedures; through differences/faults in the manufacture of electrical elements; through electrical losses; as well as variations that would be recognized by one skilled in the art as being equivalent so long as such variations do not encompass known values practiced by the prior art. Typically, the term "about" means greater or lesser than the value or range of values stated by $\frac{1}{10}$ of the stated value, e.g., ±10%.

Embodiments of the disclosure may be embodied in many different forms, including, but in no way limited to, computer program logic for use with a processor (e.g., a microprocessor, microcontroller, digital signal processor, or general purpose computer), programmable logic for use with a programmable logic device, (e.g., a Field Programmable Gate Array (FPGA) or other programmable logic device), discrete components, integrated circuitry (e.g., an Application Specific Integrated Circuit (ASIC)), or any other means including any combination thereof. In a typical embodiment of the present disclosure, some or all of the processing of the data collected using a medical monitor and the processor-based system is implemented as a set of computer program instructions that is converted into a computer executable form, stored as such in a computer readable medium, and executed by a microprocessor under the control of an operating system.

Computer program logic implementing all or part of the functionality previously described herein may be embodied in various forms, including, but in no way limited to, a source code form, a computer executable form, and various intermediate forms (e.g., forms generated by an assembler, compiler, linker, or locator). Source code may include a series of computer program instructions implemented in any of various programming languages (e.g., an object code, an assembly language, or a high-level language such as Fortran, C, C++, JAVA, or HTML) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The computer program may be fixed in any form (e.g., source code form, computer executable form, or an intermediate form) either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies (e.g., Bluetooth), networking technologies, and internetworking technologies. The computer program may be distributed in any form as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the Internet or World Wide Web).

Hardware logic (including programmable logic for use with a programmable logic device) implementing all or part of the functionality previously described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL).

Programmable logic may be fixed either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), or other memory device. The programmable logic may be fixed in a signal that is transmittable to a computer using any of various communication technologies, including, but in no way limited to, analog technologies, digital technologies, optical technologies, wireless technologies (e.g., Bluetooth), networking technologies, and internetworking technologies. The programmable logic may be distributed as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the Internet or World Wide Web).

Various examples of suitable processing modules are discussed below in more detail. As used herein a module refers to software, hardware, or firmware suitable for performing a specific data processing or data transmission task. Typically, in a preferred embodiment a module refers to a software routine, program, or other memory resident application suitable for receiving, transforming, routing and processing instructions, or various types of data such as resistance changes, voltage changes, current changes, contraction frequency, contraction strength, contraction duration, pressure values for a given contraction, fetal heart rate, mother's heart rate, period between doses, ratios, indices and other information of interest.

Computers and computer systems described herein may include operatively associated computer-readable media such as memory for storing software applications used in obtaining, processing, storing and/or communicating data. It can be appreciated that such memory can be internal, external, remote or local with respect to its operatively associated computer or computer system.

Memory may also include any means for storing software or other instructions including, for example and without limitation, a hard disk, an optical disk, floppy disk, DVD (digital versatile disc), CD (compact disc), memory stick, flash memory, ROM (read only memory), RAM (random access memory), DRAM (dynamic random access memory), PROM (programmable ROM), EEPROM (extended erasable PROM), and/or other like computer-readable media.

In general, computer-readable memory media applied in association with embodiments of the disclosure described herein may include any memory medium capable of storing instructions executed by a programmable apparatus. Where applicable, method steps described herein may be embodied or executed as instructions stored on a computer-readable memory medium or memory media. These instructions may be software embodied in various programming languages such as C++, C, Java, and/or a variety of other kinds of software programming languages that may be applied to create instructions in accordance with embodiments of the disclosure.

A storage medium may be non-transitory or include a non-transitory device. Accordingly, a non-transitory storage medium or non-transitory device may include a device that is tangible, meaning that the device has a concrete physical form, although the device may change its physical state. Thus, for example, non-transitory refers to a device remaining tangible despite this change in state.

The aspects, embodiments, features, and examples of the disclosure are to be considered illustrative in all respects and are not intended to limit the disclosure, the scope of which is defined only by the claims. Other embodiments, modifications, and usages will be apparent to those skilled in the art without departing from the spirit and scope of the claimed disclosure.

The use of headings and sections in the application is not meant to limit the disclosure; each section can apply to any aspect, embodiment, or feature of the disclosure.

Throughout the application, where compositions are described as having, including, or comprising specific components, or where processes are described as having, including or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components and can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. Moreover, the singular forms "a," "an," and "the" include plural forms unless the context clearly dictates otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions may be conducted simultaneously.

Where a range or list of values is provided, each intervening value between the upper and lower limits of that range or list of values is individually contemplated and is encompassed within the disclosure as if each value were specifically enumerated herein. In addition, smaller ranges between and including the upper and lower limits of a given range are contemplated and encompassed within the disclosure. The listing of exemplary values or ranges is not a disclaimer of other values or ranges between and including the upper and lower limits of a given range.

It is to be understood that the figures and descriptions of the disclosure have been simplified to illustrate elements that are relevant for a clear understanding of the disclosure, while eliminating, for purposes of clarity, other elements. Those of ordinary skill in the art will recognize, however, that these and other elements may be desirable. However, because such elements are well known in the art, and because they do not facilitate a better understanding of the disclosure, a discussion of such elements is not provided herein. It should be appreciated that the figures are presented for illustrative purposes and not as construction drawings. Omitted details and modifications or alternative embodiments are within the purview of persons of ordinary skill in the art.

It can be appreciated that, in certain aspects of the disclosure, a single component may be replaced by multiple components, and multiple components may be replaced by a single component, to provide an element or structure or to perform a given function or functions. Except where such substitution would not be operative to practice certain embodiments of the disclosure, such substitution is considered within the scope of the disclosure.

The examples presented herein are intended to illustrate potential and specific implementations of the disclosure. It can be appreciated that the examples are intended primarily for purposes of illustration of the disclosure for those skilled in the art. There may be variations to these diagrams or the operations described herein without departing from the spirit of the disclosure. For instance, in certain cases, method steps or operations may be performed or executed in differing order, or operations may be added, deleted or modified.

What is claimed is:

1. A device comprising:
   a maternal fetal monitor comprising:
      a contraction measurement device configured to measure a rate of uterine contractions; and
      a user interface configured to display the rate of uterine contractions;
   an infusion pump configured to administer a medication intravenously to a patient,
   wherein the rate of uterine contractions is selected from the group consisting of frequency, strength, and duration of uterine contractions,
   wherein the infusion pump administers the medication intravenously to induce and augment uterine contractions,
   wherein the device is configured to stop the administration of the medication when one or more of the frequency, strength, or duration of uterine contractions is outside predetermined ranges; and wherein the device is configured to restart the pump by the inputting of passcodes corresponding to categories of medical staff delineated by seniority and expertise, wherein each category has a set number of times to restart the pump, such that once the set number of times is met within a category, the pump cannot be restarted by a passcode of that category.

2. The device according to claim 1, wherein the device measures frequency, strength, and duration of uterine contractions at predetermined intervals.

3. The device according to claim 1, wherein the measurement device measures pressure across a patient's abdomen.

4. The device according to claim 3, wherein the measurement device is a tocodynamometer belt or intrauterine pressure catheter.

5. The device according to claim 1, wherein the infusion pump is configured to be connected to the patient via an intravenous catheter.

6. The device according to claim 1, wherein the medication is Pitocin or another form of synthetic oxytocin.

7. The device according to claim 1, wherein the device is further connected to a remote terminal, the remote terminal comprising an alarm that sounds both at external locations and in the patient's room when the rate of uterine contraction falls outside the predetermined ranges.

8. The device according to claim 7, wherein the device sounds an alarm at a remote nurses' station.

9. The device according to claim 1, wherein said device controls a power source to the infusion pump.

10. The device according to claim 9, wherein the device is configured to automatically shut off the power to the infusion pump when a patient is contracting for more than 50 percent of a predetermined period of time.

11. The device in claim 1, wherein the strength of contraction is measured from a baseline when the uterus is relaxed to the peak of a contraction.

12. The device in claim 1, wherein the contraction measurement device measures the strength of contraction by measuring one or more pressure values in or from the uterus.

13. The device in claim 12, wherein the contraction measurement device measures the strength of contraction by measuring one or more pressure values in or from the uterus in mm Hg.

14. A device comprising:
   a maternal fetal monitor comprising:
      a contraction measurement device configured to measure a rate of uterine contractions;
      a user interface configured to display the rate of uterine contractions;
   an infusion pump configured to administer a medication intravenously to a patient,
   wherein the rate of uterine contractions is selected from the group consisting of frequency, strength, and duration of uterine contractions,
   wherein the infusion pump administers the medication intravenously to induce and augment uterine contractions,
   wherein the device is configured to stop the administration of the medication when one or more of the frequency, strength, or duration of uterine contractions is outside predetermined ranges; and wherein the device is configured to restart the pump by the inputting of passcodes
   corresponding to one or more categories of medical staff, wherein each of the one or more categories has a set number of times to restart the pump, such that once the set number of times is met within a category, the pump cannot be restarted by a passcode of that category.

* * * * *